United States Patent [19]
Linden

[11] Patent Number: 5,626,151
[45] Date of Patent: May 6, 1997

[54] TRANSPORTABLE LIFE SUPPORT SYSTEM

[75] Inventor: Charles Linden, Bethesda, Md.

[73] Assignee: The United States of America as represented by the Secretary of the Army, Washington, D.C.

[21] Appl. No.: 610,823

[22] Filed: Mar. 7, 1996

[51] Int. Cl.$^6$ ................................................ A61G 1/02
[52] U.S. Cl. ............................................................ 128/897
[58] Field of Search ............................... 5/625; 128/897, 128/3, 906, 202.16

[56] References Cited

U.S. PATENT DOCUMENTS

| | | | |
|---|---|---|---|
| 4,352,991 | 10/1982 | Kaufman | 307/9 |
| 4,584,989 | 4/1986 | Stith | 128/897 |

*Primary Examiner*—William E. Kamm
*Assistant Examiner*—Scott M. Getzow
*Attorney, Agent, or Firm*—John Francis Moran

[57] ABSTRACT

A transportable life support system is for use in a battlefield and mass casualty situations and includes a base, a stretcher and a canopy. The base incorporates medical equipment that includes a ventilator, an oxygen source, an environmental control unit, a suction unit, a plurality of physiologic sensors, a intravenous fluid pump, a drug infusion pump, and a defibrillator. The medical equipment is controlled by a computer contained within the base. A monitor displays the vitals signs of the wounded patient. A receiver/transmitter is included in the base for transmitting information to, and receiving information from, a remote health care provider. The system can be run from internal rechargeable batteries or external power. The canopy may be a hard shell or a soft shell. With the canopy in place, the transportable life support system serves as a miniature preoperative holding area or a post operative recovery room. Furthermore, with the canopy in place, the environmental control unit provides positive overpressure to protect against chemical/biological contamination. With the canopy off, the transportable life support system serves as a self-contained operative platform for use in military or natural disaster settings.

89 Claims, 5 Drawing Sheets

TRANSPORTABLE LIFE SUPPORT SYSTEM

The present invention is a stretcher-based mini-intensive care unit that incorporates resuscitative and life-sustaining capabilities into a universally adaptive platform for trauma management and unattended patient support. It allows the transport of medically unstable patients and fits into existing evacuation platforms.

BACKGROUND OF THE INVENTION

Since the end of World War I, the mortality rate for U.S. Army combat casualties is near 20% and has not changed significantly in spite of dramatic advances in medical technology. This is because 90% of all combat related deaths occur within the first hour after injury on the battlefield. One of the major goals of the Army's medical department is to decrease the mortality rate from combat injuries by providing the medical capability necessary to manage life threatening injuries. Thus, the transportable life support system was designed to project intensive care capability to assess and treat trauma victims as close to the site of injury as possible, provide mobile pre-operative and post-operative intensive care capability under extreme environmental conditions, and serve as a surgical platform.

Another major goal of the Army's medical department is to decrease the footprint of medical facilities on the battlefield. A significant portion of medical assests are currently consumed by post surgical patients, which according to current Army doctrine, must be stable prior to evacuation. This requirement results in a significant logistical burden to ground forces and is principally driven by the fact that there are no effective monitoring or therapeutic capabilities during ground or air transport which allow one to detect and respond to a life threatening medical emergency should one occur en route to a definitive care treatment facility. Thus, another goal of the transportable life support system is to decrease the medical footprint on the battlefield by providing the necessary therapeutic and physiologic monitoring capability needed to evacuate the potentially unstable patient.

In addition to battlefield applications, the transportable life support system can serve in the civilian sector as a medical assest during natural disasters or mass casualty scenarios where medical personnel and medical equipment resources are limited or not available.

Several stretcher based devices have been developed to enhance a caretaker's ability to monitor and treat patients in critical condition during transport or in remote areas where conventional medical assests are not available. For example, the MOBILE INTENSIVE CARE RESCUE FACILITY (MIRF) is a portable stretcher-based intensive care monitoring system designed by Buchanan Aircraft Corporation. It contains (i) a physiologic monitoring system, (ii) a ventilator, (iii) a volumetric infusion pump for fluid resuscitation, (iv) a syringe pump for drug administration, (v) a suction unit, (vi) a defibrillator, (vii) two oxygen tanks, and (viii) a battery power supply capable of maintaining stand-alone operation for 2 hours. The MIRF houses the medical equipment in a fiberglass bay which fits beneath the stretcher. The sides of the bay are open and allow access to the medical equipment.

Similar to the MIRF, the CARE FLIGHT STRETCHER BRIDGE for aeromedical transport of the critical care patient is a multi-story tray mounted to a stretcher. The unit contains 2 infusion pumps, a ventilator, a physiologic monitoring system, a defibrillator, an oxygen tank (6 cylinder with regulator), and a suction device. Additional resuscitation equipment is carried in an additional transport backpack.

Although similar in design, the MOBILE INTENSIVE CARE PATIENT HANDLING TRANSPORT APPARATUS (U.S. Pat. No. 4,957,121) was constructed to accomadate the needs of patients in heart failure requiring transport. It consists of a cot and a detachable pallet containing medical equipment that attaches underneath the framework of the cot. The medical equipment includes a power source with battery back-up, an intra-aortic balloon pump, a ventilator, an infusion pump, a physiologic monitoring system, a defibrillator, and a patient restraint system.

Another device designed for the transport of patients with severe cardiac illness is the HEART-LUNG RESUSCITATOR LITTER (U.S. Pat. No. 4,060,079) which is a portable stretcher that provides external chest compressions, oxygen, and an iv pole.

Simplified versions of the same type of equipment include the PORTABLE LIFE SUPPORT SYSTEM, (U.S. Pat. No. 4,352,991) and the RESCUE UNIT (U.S. Pat. No. 4,389,066). The PORTABLE LIFE SUPPORT SYSTEM contains a stretcher and a DC power supply. It may contain additional equipment to include a defibrillator, a suction device, components of an intravenous line, oxygen tank regulators, and a physiologic monitoring system. Similarly, the RESCUE UNIT is a vehicle that has beed built to be towed by snowmobile. The device contains a patient and attendant section and includes a suction unit, lights, first aid kit, battery power source, two way radio, heating element, horn, canopy to cover the patient, and patient call button.

While the above references are directed to providing stretcher based assitance to an injured patient, they do not provide the degree of medical care that the present invention does. In addition to physiological monitoring, ventilation, defibrillation, stand alone power, an oxygen source, and fluid infusion pumps, the life support system includes autonomous fluid resuscitation and ventilation that allow appropriate therapy to continue under conditions where trained personnel are not available.

Servo control systems for the delivery of fluid and medications have been well established as shown in APPARATUS FOR THE BIOFEEDBACK CONTROL OF BODY FUNCTIONS, U.S. Pat. No. 5,002,055, INFUSION PUMP CONTROLLER, U.S. Pat. No. 4,392,849, but they have not been a part of the stretcher based portable mini-intensive care unit as the present invention discloses. The transportable life support system also includes a communication system that allows remote control of diagnostic and therapeutic components of the system, if qualified personnel are not available on site; ability to fit within a variety of evacuation vehicles (fit within a 72" long by 22" wide by 18" high space) yet still allow access to medical equipment even if one or more sides of the base is blocked; size and weight constraints that make it manageable to carry with a patient in rough terrain; and an environmental control unit that filters and controls the temperature of circulating air.

With the canopy in place, the transportable life support system serves as a protected, temperature controlled pre-operative "waiting room", a post-operative intensive care unit before and during evacuation, and a protective barrier from biological and chemical agents while allowing patient treatment. Devices that provide contamination from life threatening substances (ANIT-CONTAMINATION MEANS, U.S. Pat. No. 4,736,762) and providing control of a patient's environment in a stretcher configuration (LIFE SUPPORT CHAMBER FOR INFANTS, METHOD AND SYSTEM, U.S. Pat. No. 4,161,172) have been developed, but do not contain the suite of physiologic monitoring systems and therapeutic devices contained in the transportable life support system of the present invention.

With the canopy removed, the Transportable Life Support System serves as a surgical platform much like the PORTABLE SURGICAL TABLE (U.S. Pat. No. 5,375,276), but also includes the necessary physiologic monitoring required for surgical procedures.

SUMMARY OF THE INVENTION

It is therefore an object of the present invention to provide trauma care to an injured patient as far forward in a battlefield or mass casualty situation, as possible.

It is another object of the present invention to deliver advanced trauma care to an injured patient within the first hour of injury.

It is another object of the present invention to disclose a transportable life support system comprising a base, a stretcher and a canopy.

It is another object of the present invention to disclose a transportable life support system having a ventilator, an oxygen source, a thermal control unit, a defibrillator and a suction unit.

It is another object of the present invention to disclose a transportable life support system that is controlled by a computer locally or remotely.

It is another object of the present invention to disclose a transportable life support system that displays the vital signs of the patient locally or remotely.

It is another object of the present invention to disclose a transportable life support system that provides a non-invasive physiologic monitoring system, an automatically or manually controlled fluid resuscitation and drug delivery system that provides fluid resuscitation and drug delivery to an injured person.

It is another object of the present invention to disclose a communication telemetry system and a monitor screen that provides information regarding an injured persons vital signs both locally and remotely.

The object of the present invention are realized by disclosing a stretcher having a base which has a fluid impermeable seal. The base contains medical equipment that includes a ventilator, a defibrillator, an oxygen source, a suction unit, a high volume infusion pump, a low volume infusion pump, a physiological monitoring system, a battery pack, a power conversion system, an environmental control unit, an on-board computer system, a monitor, and a communications telemetry system.

The medical equipment can utilize power from a variety of sources such as internal batteries or external power sources. The on-board computer can gather data from the physiologic monitoring system to provide closed loop control of the medical equipment to deliver autonomous hemodynamic and ventilatory support when a health care provider resources are limited or not available. The vital signs of the patient can be displayed on a monitor or transmitted to remote medical staff via the communications telemetry system. The remote medical staff can transmit instructions to either the attending physician or medic or to the on-board computer.

The fluid resuscitation system, of the present invention, operates with the transportable life support system by monitoring physiological parameters in order to deliver resuscitation fluid and drugs to the injured patient, when needed.

The various components that are used in the present invention are capable of easily being replaced. The sensors, pumps, and monitors of the present invention are individually sealed units each having an interface port to connect with the on-board computer. When these units are damaged or become outdated, they are disconnected from the on-board computer and replaced by a new unit.

The stretcher of the present invention can be easily detached from the base. The canopy of the present invention, forms a relatively airtight seal with the base in order to provide environmental protection and protection from chemical/biological contaminants.

As part of the physiologic monitoring system, the base and/or a component of the stretcher itself contains at least one non-invasive temperature sensor that will monitor the temperature of the patient and/or the environment surrounding the patient. The temperature information is used to adjust the environment control unit in order to obtain and maintain a target patient temperature.

The present invention provides mobile intensive care for acute management of trauma victims, preoperative holding, intraoperative monitoring, post operative recovery, and patient evacuation.

DETAILED DESCRIPTION

The present invention is part of an overall Army effort to improve the medical care delivered in the field. Since WW I, the percentage of combat mortality has remained between 20–25%, with 90% of the battle related deaths occurring on the battlefield. The goal is to bring levels of care currently available only in rear echelons to forward positions where they can play a role in the acute management of life threatening injuries. The transportable life support system of the present invention has application in any situation requiring medical care, where medical facilities are not easily available.

Figure 1:
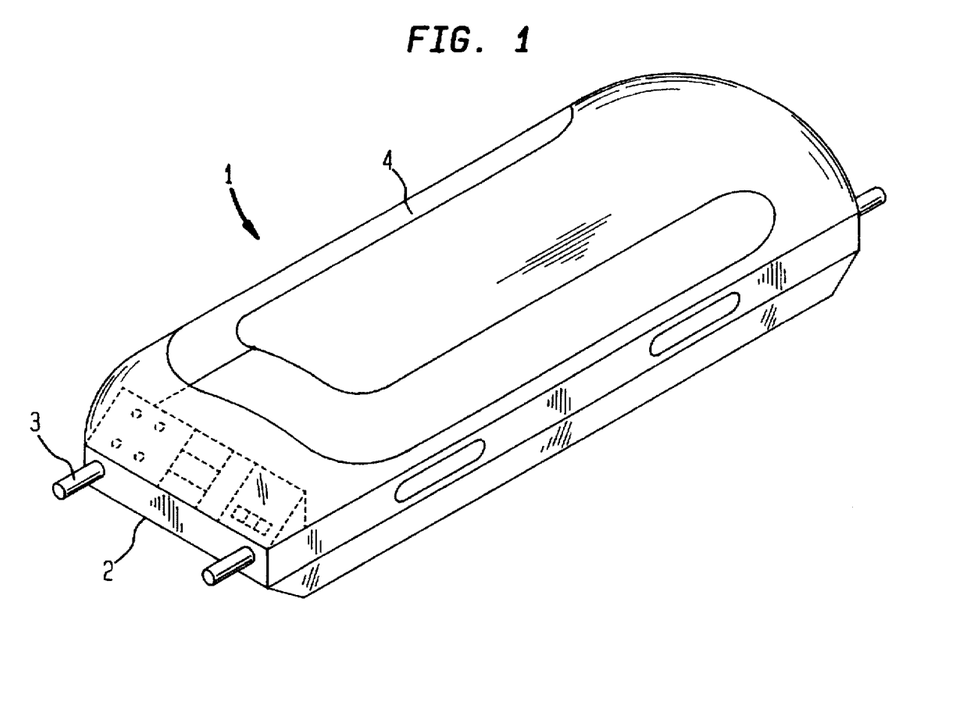
FIG. 1 is an elevated perspective view of the transportable life support system of the present invention.

FIG. 1 illustrates the transportable life support system 1 of the present invention. The system 1 has a base 2, a stretcher 3, and a canopy 4.

The base 2 is constructed from a composite shell in order to provide a protective and durable housing for medical equipment. The base 2 may be constructed from fiber reinforced resin composites, graphite composites, ceramic alloys, metallic alloys, or composites thereof.

The result is a base 2 that is strong, impact resistant, and light-weight. The base 2 can withstand high impact situations without fracturing, delaminating, or permanently deforming. The base 2 is protected with a polymeric or metal matrix coating that is resistive to environmental contaminants and to chemical/biological agents and contains material which provides electromagnetic interference shielding. The base 2 is also impervious to gas absorption and subsequent outgassing. All traces of a chemical/biological attack may be removed from the base 2 by wiping the base 2 clean or "hosing down" the device 1. Base 2 may be additionally configured to conform to existing stretcher configurations.

A stretcher 3 can be easily detached from the base 2. The stretcher 3 is removed from the base 2 to retrieve injured patients. The stretcher 3 containing the injured patient is then returned and attached to the base 2 so that the patient can receive medical attention. In the preferred embodiment, the stretcher 3 would meet the standards set by NATO for stretchers.

Figure 2:
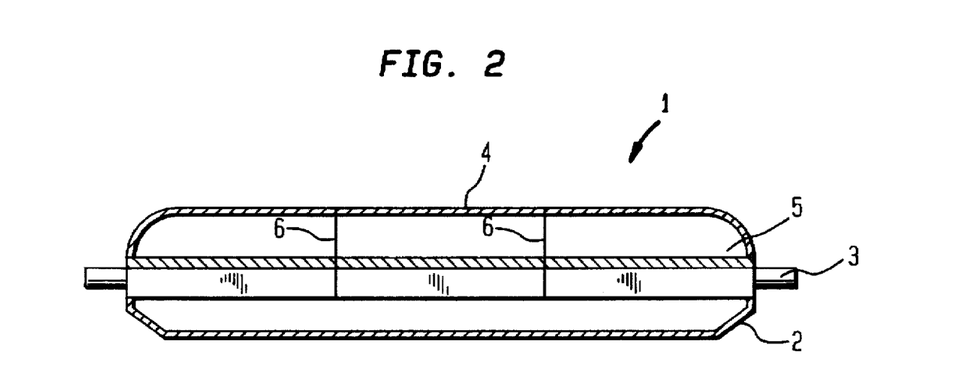
FIG. 2 is a cross-sectional side-view of the transportable life support system of the present invention.

As illustrated in FIG. 2, a heating/cooling pad 5 may be placed on stretcher 3. The pad 5 noninvasively monitors and controls the patient's core temperature, by indirectly warming or cooling the patient as necessary.

A canopy 4 may be used to cover the patient. The canopy 4 may have a hard shell. A hard shell canopy 4 would protect the patient from ballistics. Also, the canopy 4 may be constructed of a soft shell material. In either case, the canopy 4 would protect the patient from chemical/biological contamination by forming a relatively air-tight seal with the base 2.

Figure 2A:
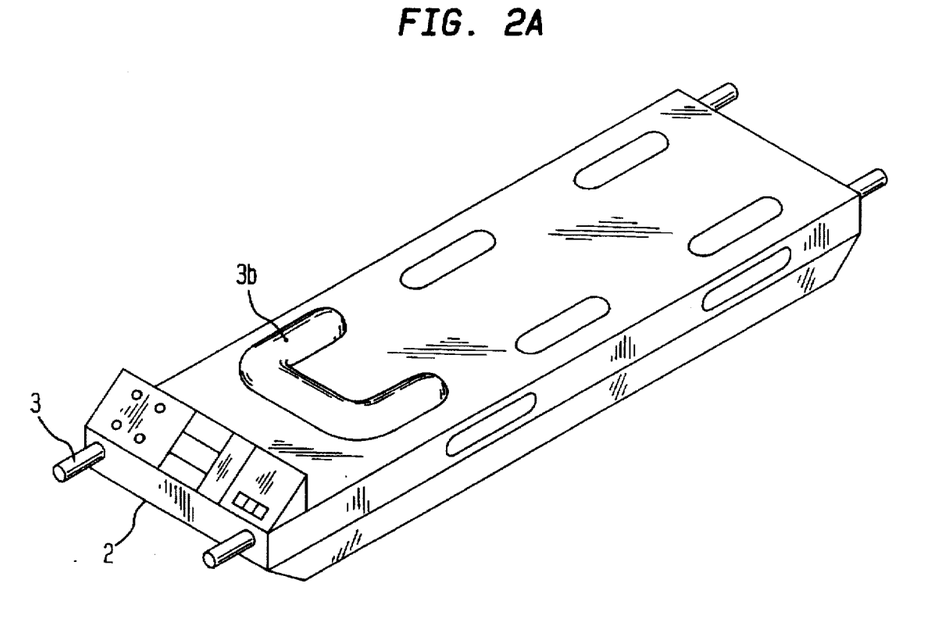
FIG. 2a is a top view of the transportable life support system with the stretcher having a spinal board and cervical collar

A soft shell canopy 4 would be supported by supports 6 as illustrated in FIG. 2. The soft shell canopy 4 would contain pleats in order to expand to accommodate a patient wearing boots and a helmet. Certain injuries (e.g., spinal injuries) mandate that the patient's helmet not be removed. Additionally, as shown in FIG. 2a a spine board 3a and cervical collar 3b may be incorporated into the stretcher 3 to further stabilize patients having spinal injuries.

Figure 3:
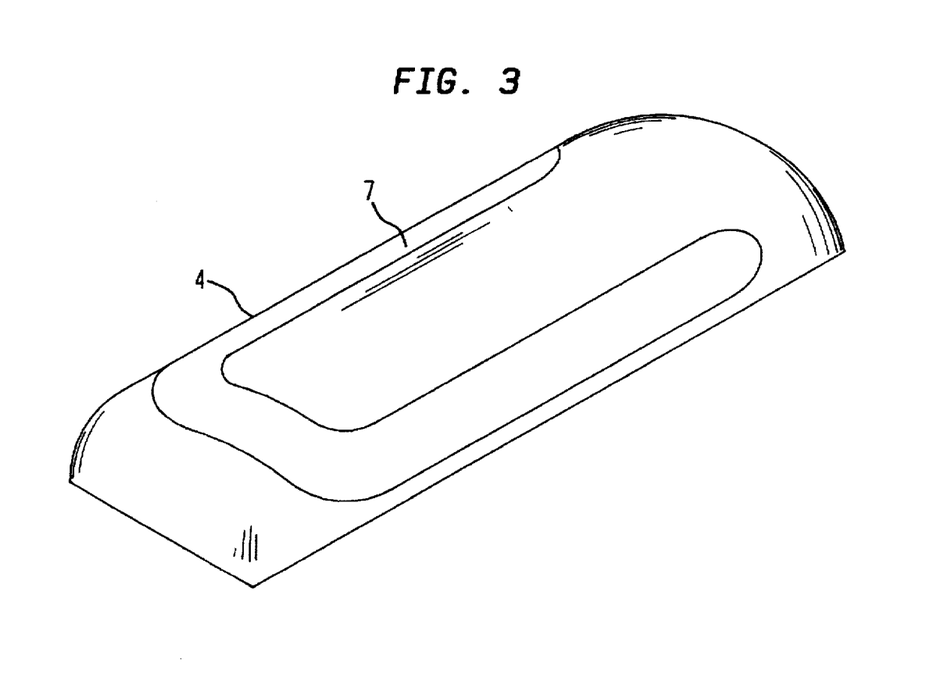
FIG. 3 is a top view of the canopy of the present invention.

To prevent the greenhouse effect from overheating the patient, the canopy 4 is opaque with the canopy 4 having reflective and insulating properties. To facilitate visual access to the patient, a window 7 as illustrated in FIG. 3 would be provided in the canopy 4. The window 7 may be made out of clear plastic coated to block out infrared and ultraviolet light. The window 7 may extend the whole length of the canopy 4 along both sides of the patient and around the head of the patient.

Figure 4:
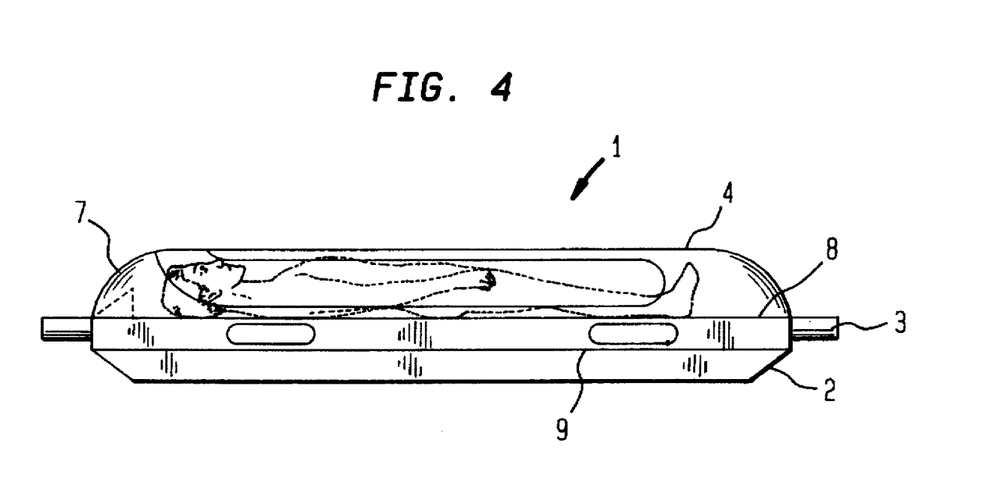
FIG. 4 is a side view of the canopy of the present invention.

To allow physical access to the patient, a fastening means 8 as illustrated in FIG. 4 may be included in the canopy 4. Fastening means 8 include zippers, two-headed zippers, Velcro fastener snaps, etc. to allow quick access to the patient.

In the preferred embodiment, the canopy 4 is made of a pliable material which is a three layer laminate having a saran middle layer sandwiched between reflective and insulative high density polymeric layers. This material provides protection from the environment as well as from chemical and biological contamination.

The canopy 4 attaches to the base 2 to form a relatively fluid-tight seal 9 as illustrated in FIG. 4. Any exchange between the inside of the system 1 and the outside environment, be it air, oxygen, liquid, or electricity, must go through corresponding apertures in the base 2.

Figure 5:
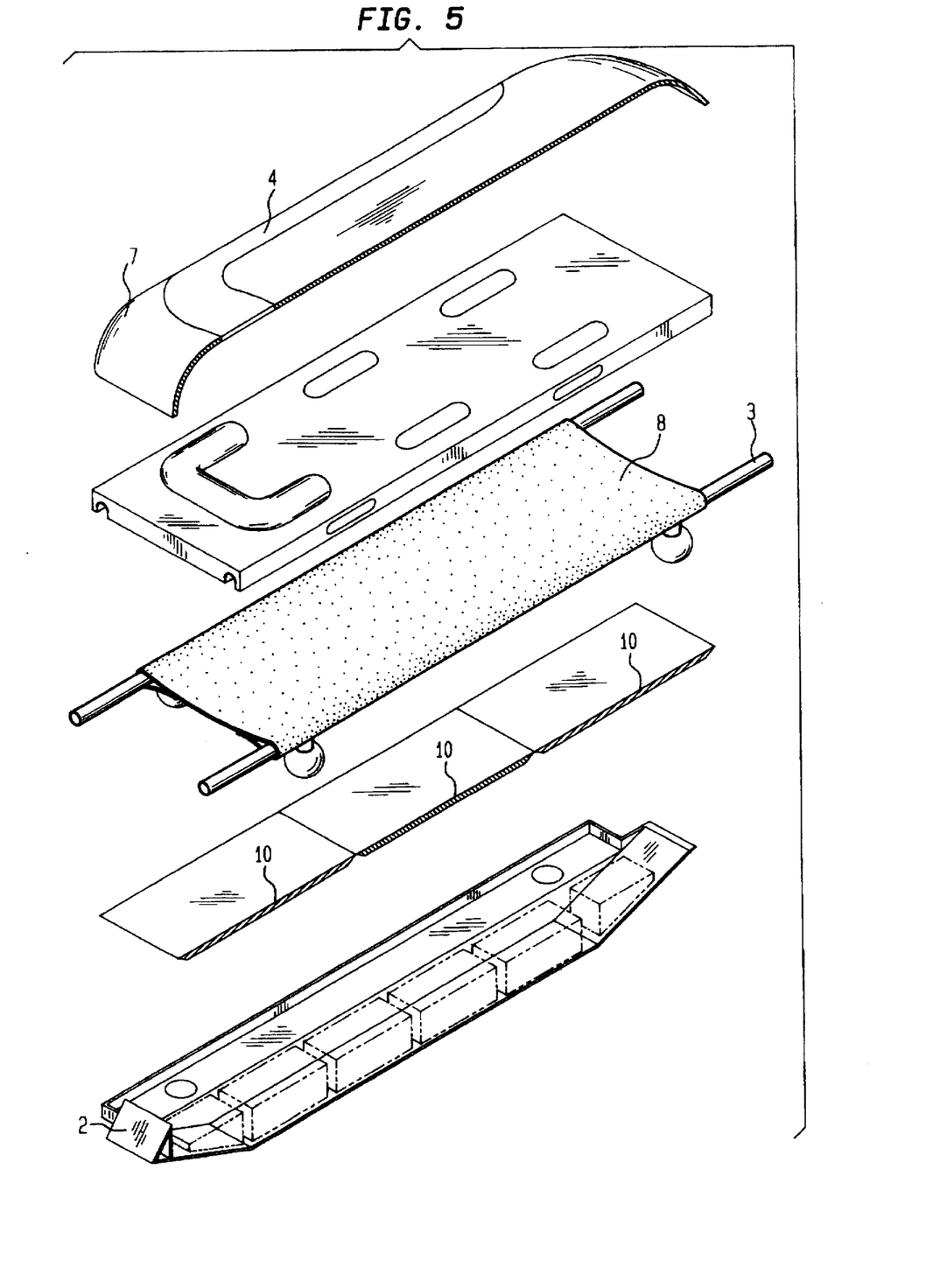
FIG. 5 is an exploded cross-sectional side-view of the present invention.

The base 2 houses medical equipment. As illustrated in FIG. 5, the base 2 includes panels 10 that allow access to the medical equipment contained within the base 2. When closed, the panels 10 form a barrier that does not allow fluids to come in contact with the medical equipment. Fluids spilled on the base 2 can be cleaned off using conventional cleaning materials.

Figure 6:
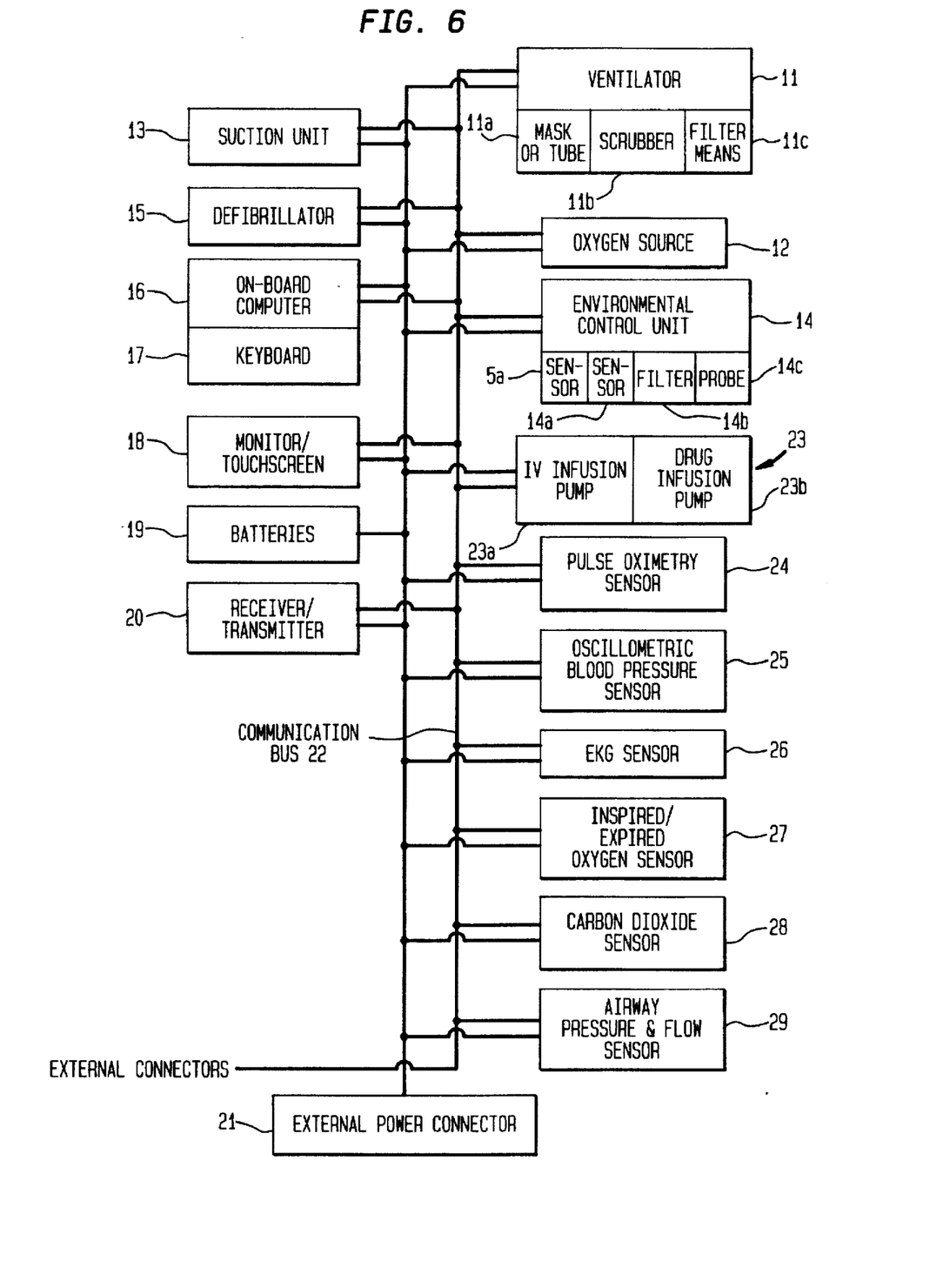
FIG. 6 is a schematic of the medical equipment contained within the base of the present invention.

As illustrated in FIG. 6, the medical equipment housed within the base 2 includes a ventilator 11, an oxygen source 12 such as an oxygen tank or an oxygen generator, a suction unit 13, an environmental control unit 14, and a defibrillator 15. The base 2 also houses an on-board computer 16, an input device or a keyboard 17, monitor/touch screen 18, batteries 19, a receiver/transmitter 20, an external power connector 21, a communication bus 22, a pump system 23 which includes a high volume intravenous (hereinafter referred to as iv) infusion pump 23a and a low volume drug infusion pump 23b, a pulse oximetry sensor 24, an oscillometric blood pressure sensor 25, an electrocardiogram sensor 26, an inspired/expired oxygen sensor 27, an inspired/expired carbon dioxide sensor 28, and an air way pressure sensor 29. The communication bus 22 connects all of the components of the present invention. External signals for communicating with the on-board computer 16 and controlling the other components of the present invention are routed through the communication bus 22.

The ventilation system is driven by the ventilator 11 which draws in air that is external to the system 1, combines the external air with oxygen from the oxygen source 12, and delivers it into the patient. The on-board computer 16 determines the need for oxygen delivery based on arterial hemoglobin oxygen saturation levels measured by a pulse oximeter sensor 24 and conserves the oxygen supply by delivering oxygen to the patient only during inspiration. A means for supplying and maintaining delivery of air 11a is used to direct air down the trachea to the lungs of the patient. Such a means includes a laryngeal mask airway or an endotracheal tube. The means for supplying and maintaining delivery of air 11a keeps the breathing air separate from the circulating warm or cool air. The circulating air system is controlled by the environmental control unit 14, as will be discussed hereinbelow. The ventilator 11 may include a carbon dioxide scrubber 11b to remove carbon dioxide from expired air. The ventilator 11 includes a means for filtering intake and exhaust air of contaminants present in the air stream. The filtering means may be in the form of at least one filter 11c, and are generally of "NBC"-type filters.

The oxygen source 12 for the patient, may include oxygen tanks or an oxygen generator which allows the present invention to be used in situations where oxygen is not available and/or the air supply is contaminated (e.g., chemical or biological contamination). When using an oxygen generator, system 1 does not require an external source of oxygen. Delivery of oxygen to the patient, from the oxygen source 12, is determined by the on-board computer 16 based on hemoglobin saturation measurements from the pulse oximetry sensor 24.

The suction unit 13 is used to remove unwanted fluids from the patient's airway or from the surgical field.

The environmental control unit 14 is used to control the patient's body temperature in one of two ways. The environmental control unit 14 controls or maintains a desired body temperature by cooling or warming the patient. A temperature sensor 14a is used to measure the patient's body temperature. Temperature sensor 14a may be an axillary probe, a rectal probe, or a tympanic sensor. To control the body temperature, the on-board computer 16 determines a body set-point temperature and gradually increases or decreases the temperature using the environmental control unit 14, while continuously monitoring the effect of the changing temperature on the patient's body temperature.

The first of the two ways used by the environmental control unit 14, includes placing the patient on the heating/ cooling pad 5 which warms or cools the patient as necessary. The heating/cooling pad 5 may further include a thermally controlled fluid circulated through the pad 5 to control the body temperature of the patient. The temperature of pad 5 is monitored through a temperature sensor 5a. The on-board computer 16 compares the patient's temperature reading with a set point temperature, and gradually increases or decreases the temperature of the heating/cooling pad 5, while continuously monitoring the effect on the patient's body temperature.

The second of the two ways used by the environmental control unit 14 includes control of the patient's body temperature by cooling (or warming) the air circulating around the patient. The environmental control unit 14 includes a means for providing contaminant-free air to the unit. The means may be in the form of at least one filter 14b, and are generally of "NBC"-type filters. An air temperature probe 14c, which may be a thermocouple or a thermistor type probe, is used to measure the temperature of the air coming out of the system 1. This measurement is utilized to determine the efficiency of the air circulating around the patient and to provide on-board computer 16 with a temperature reading of system 1. On-board computer 16 compares the temperature reading within system 1 with a set point temperature, and gradually increases/decreases the temperature of the air in system 1 while continuously monitoring the effect on the patient's body temperature.

A defibrillator 15, is utilized to provide cardioversion to correct life threatening arrhythmias.

A specific purpose of the transportable life support system includes use by a medic who only has basic medical training. The on-computer 16 is capable of automatically executing algorithms to monitor physiological parameters and adjusting settings on various pieces of equipment housed within base 2. The on-board computer 16 transmits a signal that can be recognized by a global positioning system. The global positioning signal from the on-board computer 16 is then used to pinpoint the location of the transportable life support system 1. The format of signals transmitted by the on-board computer 16 are compatible with the international data exchange standard. The input device 17 is connected to the on-board computer 16 to allow the attending medic or physician to override the automatic control of the computer 16 in order to manually control the various equipment and manually administer medical treatment.

The on-board computer 16 further includes a data display monitor 18 for informing the attending medic or physician of the status of the patient's vital signs, history of infusion pumps 23a and 23b, and the history of the ventilator 11. The monitor/touch screen 18 provides the attending medic or physician with an alternative method of overriding the automatic control of the on-board computer 16. The touch screen feature of the monitor 18 also allows the attending medic or physician to display the patient's vital signs.

The present invention includes a receiver/transmitter 20 that allows the vital signs and other medical data from the patient to be sent to a remote location for analysis. A physician at the remote location may then send instructions to the on-board computer 16 to directly adjust such parameters as ventilator 11 settings, iv fluid infusion rates and/or drug infusion rates, etc., or send messages back to the attending medic or physician. The receiver/transmitter 18 may include a radio-frequency modem.

The present invention may be powered by a power source such as internal batteries 19 or by an external power source 21. The external power source may be supplied by a direct current, or alternating current power source as may be found in existing air and ground vehicles and gas/diesel powered generators. The system 1 is also capable of operation at any location around the world as it is capable of incorporating power supplies existing anywhere in the world through existing power conversion apparatus and stabilization technology. Whenever the system 1 is running from the external power source 21, the internal batteries 19 would be charging. The internal batteries 19 may be used to run or charge external medical equipment. In an alternate embodiment, the present invention may include fuel/solar cells, as a source of electrical power.

The infusion pumps 23a and 23b are used to provide resuscitation fluid and drugs, to the patient. Feedback from measured physiologic parameters is used by the on-board computer 16 to provide autonomous control of the IV and drug infusion pumps 23a and 23b. A physician or medic may override the autonomous control of pumps 23a and 23b and manually control them locally or remotely.

The pulse oximetry sensor 24 is used to measure the patient's blood oxygen saturation level. The sensor 24 is a non-invasive-type sensor which may be positioned on the patient's finger, toe or earlobe. Pulse oximetry sensors are generally known and commercially available.

The oscillometric blood pressure sensor 25 is used to periodically monitor the patient's blood pressure. Sensor 25 is a non-invasive-type sensor which may be positioned on the patient's arm or finger. Oscillometric blood pressure sensors are generally known and commercially available. Other non-invasive blood pressure monitoring methods may also be incorporated.

The electrocardiogram sensor 26 is used to continuously monitor the patients heart rate. Sensor 26 is a non-invasive type sensor which is positioned on the patient's chest. Electrocardiogram sensors are generally known and commercially available.

The inspired/expired oxygen sensor 27 is used to measure oxygen levels within the patent's airway. Information from this sensor 27, in conjunction with the pulse oximetry sensor 24, is used by the on-board computer 16 to deliver oxygen to the patient when needed. The sensor 27 is positioned within the patient's endotracheal tube (or airway circuit).

The carbon dioxide sensor 28 is similar to the inspired/expired oxygen sensor 27, and is used to measure carbon dioxide within the airway. Information from this sensor 28 can be used to diagnose airway or pulmonary problems to include improperly placed endotracheal tube or a tension pneumothorax. The sensor 28 is positioned within the patient's endotracheal tube (or airway circuit). Carbon dioxide sensors are generally known and commercially available.

The airway pressure sensor 29 is used to place a high and low pressure limit on the ventilator 11 to prevent the deleterious effects of over or under inflation. The sensor 29 is positioned within the patient's endotracheal tube (or airway circuit). Airway pressure sensors are generally known and commercially available.

As shown in FIG. 6, a communication bus 22 connects the various equipment and sensors of system 1 together with data being channeled to a central processing unit which controls data display and storage functions.

The method employed by the transportable life support system 1 is as follows. To provide ventilator support to a critically injured patient, if necessary, providing supplemental oxygen to the patient using the ventilator 11 and the oxygen source 12; measuring and controlling the patient's temperature, if necessary, using the environmental control unit 14; removing unwanted fluids, if necessary, using the suction unit 13; defibrillating the patient, if necessary, using the defibrillator unit 15; continuously monitoring hemoglobin oxygen saturation level, using the pulse oximetry sensor 24; continuously monitoring the patient's heart rate, using the electrocardiogram sensor 26; continuously monitoring inspired/expired oxygen content using the inspired/expired oxygen sensor 27, which together with a tidal volume measurement is used to calculate oxygen delivery and oxygen consumption; continuously monitoring placement and patency of an endotracheal tube positioned in the patient's airway and monitoring the adequacy of ventilation and carbon dioxide production using the carbon dioxide sensor 28; continuously monitoring the pressure limits on the ventilator 11 (hypo and/or hyperinflation) and monitoring pulmonary compliance using the air way pressure sensor 29; continuously monitoring air flow to validate air volume delivery, allow calculation of the tidal volume and pulmonary compliance, and to provide alarms for inadequate flow rates; periodically measuring the patient's blood pressure, using the oscillometric blood pressure sensor 25, or continuously calculating a person's blood pressure using the pulse wave transmission technique, which is an estimate of blood pressure based on the time difference between the R-wave of the monitored electrocardiogram and the peak of the peripheral arterial wave form detected by the pulse oximeter; calibrating estimated blood pressure based upon oscillometric blood pressure measurements from the previous step, and administering a resuscitation fluid to the patient in a closed loop fashion using calibrated continuous blood pressure measurements as feedback to drive the fluid and drug infusion pumps 23a and 23b.

The transportable life support system including the equipment described hereinabove, may be controlled automatically by the on-board computer 16, controlled manually by an attending medic or physician, or controlled manually by a remote medic or physician. To aid the manual control of the IV infusion pump 23a, drug infusion pump 23b, the ventilator 11 and the environmental control unit 14, these parameters are displayed locally to the attending medic or physician or are transmitted to the remote medic or physician.

The present invention, allows the medic or physician to provide life supporting techniques and consult with remote medical staff. With the canopy 4, the system 1 provides a stable, pre preoperative or post operative recovery platform that simulates an intensive care environment. With the canopy off, the system 1 serves as a self-contained platform during surgical procedures.

What is claimed is:
1. A transportable life support system comprising:
   a) a base including:
      i) a ventilator having a means for supplying and maintaining delivery of air, said means constructed so as to direct air down a patient's trachea and lungs, said ventilator may or may not have a carbon dioxide scrubber constructed so as to remove carbon dioxide from expired air when rebreathing of carbon dioxide may be a hazard, a means for filtering intake and exhaust air of contaminants, said ventilator constructed so as to ventilate said patient;
      ii) an oxygen source connected to said ventilator, said oxygen source constructed so as to provide oxygen to said patient;
      iii) an environmental control unit having a means for providing contaminant-free air to the unit, said unit constructed so as to control said patient's temperature;
      iv) a suction unit constructed so as to remove unwanted fluids from the patient;
      v) a defibrillator constructed so as to provide cardioversion for correcting life threatening arrhythmias;
      vi) a monitor comprising a touch screen constructed so as to display vital signs of the patient;
      vii) a receiver/transmitter connected to said monitor, said receiver/transmitter constructed so as to transmit information to, and receive information from, a remote location;
      viii) an on-board computer connected to said ventilator, said oxygen source, and said environmental control unit, said monitor and said receiver/transmitter so as to control care administered to the patient; and
      ix) a power source constructed to operate said ventilator, said oxygen source, said environmental control unit, said suction unit, said defibrillator, said on-board computer, said monitor and said receiver transmitter;
   b) a stretcher removably attached to the base; and
   c) a canopy connected to the base, said canopy and base constructed so as to form a fluid impermeable seal.

2. The device of claim 1, wherein said means for supplying and maintaining delivery of air is selected from a group consisting of a laryngeal mask airway and an endotracheal tube.

3. The device of claim 2, wherein said means for filtering intake and exhaust air of contaminants in said ventilator and said means for providing contaminant-free air to the environmental control unit comprise at least one NBC type filter.

4. The device of claim 3, wherein said oxygen source is an oxygen generator.

5. The device of claim 4, where said environmental control unit further comprises a body temperature sensor.

6. The device of claim 5, where said body temperature sensor is selected from a group consisting of an axillary probe, a rectal probe, and a tympanic sensor.

7. The device of claim 6, wherein said power source further comprises at least one rechargeable battery and a connector constructed so as to receive external power and where said connector is connected to said at least one battery.

8. The device of claim 7, wherein said canopy comprises a hard shell.

9. The device of claim 8, where said environmental control unit comprises a heating/cooling pad.

10. The device of claim 9, where said heating/cooling pad further comprises a temperature sensor, said temperature sensor constructed so as to provide said on-board computer with a temperature reading of said heating/cooling pad.

11. The device of claim 10, where said heating/cooling pad further includes a thermally-controlled fluid constructed so as to circulate through said pad.

12. The device of claim 8, where said environmental control unit further comprises a temperature probe, said temperature probe constructed so as to measure the temperature of air circulating within said transportable life support system.

13. The device of claim 12, where said temperature probe is selected from a group consisting of a thermocouple and a thermistor.

14. A transportable life support system comprising:
   a) a base including:
      i) a ventilator having a means for supplying and maintaining delivery of air, said means constructed so as to direct air down a patient's trachea and lungs, said ventilator may or may not have a carbon dioxide scrubber constructed so as to remove carbon dioxide from expired air when rebreathing of carbon dioxide may be a hazard, a means for filtering intake and exhaust air of contaminants, said ventilator constructed so as to ventilate said patient;

ii) an oxygen source connected to said ventilator, said oxygen source constructed so as to provide oxygen to said patient;

iii) an environmental control unit having a means for providing contaminant-free air to the unit, said unit constructed so as to control said patient's temperature;

iv) a suction unit constructed so as to remove unwanted fluids from the patient;

v) a defibrillator constructed so as to provide cardioversion for correcting life threatening arrhythmias;

vi) a monitor comprising a touch screen constructed so as to display any vital signs of the patient;

vii) a receiver/transmitter connected to said monitor, said receiver/transmitter constructed so as to transmit information to, and receive information from, a remote location;

viii) an on-board computer connected to said ventilator, said oxygen source, and said environmental control unit, said monitor and said receiver/transmitter so as to control care administered to the patient; and ix) a power source constructed to operate said ventilator, said oxygen source, said environmental control unit, said suction unit, said defibrillator, said on-board computer, said monitor and said receiver transmitter;

b) a stretcher removably attached to the base; and c) a canopy connected to the base said canopy and base constructed so as to form a fluid impermeable seal.

15. The device of claim 14, wherein said means for supplying and maintaining delivery of air is selected from a group consisting of a laryngeal mask airway and an endotracheal tube.

16. The device of claim 15, wherein said means for filtering intake and exhaust air of contaminants in said ventilator and said means for providing contaminant-free air to the environmental control unit comprise at least one NBC type filter.

17. The device of claim 16, wherein said oxygen source is an oxygen generator.

18. The device of claim 17, where said environmental control unit further comprises a body temperature sensor.

19. The device of claim 18, where said body temperature sensor is selected from a group consisting of an axillary probe, a rectal probe, and a tympanic sensor.

20. The device of claim 19, wherein said power source further comprises at least one rechargeable battery and a connector constructed so as to receive external power and where said connector is connected to said at least one battery.

21. The device of claim 20, wherein said canopy comprises a soft shell.

22. The device of claim 21, wherein said soft-shell canopy is opaque and constructed so as to comprise reflective and insulative properties.

23. The device of claim 22, wherein said soft-shell canopy further comprises a clear plastic window.

24. The device of claim 16, wherein said soft-shell canopy further comprises pleats.

25. The device of claim 24, wherein said soft-shell canopy further comprises at least one fastening means.

26. The device of claim 25, where said environmental control unit comprises a heating/cooling pad.

27. The device of claim 26, where said heating/cooling pad further comprises a temperature sensor, said temperature sensor constructed so as to provide said on-board computer with a temperature reading of said heating/cooling pad.

28. The device of claim 27, where said heating/cooling pad further includes a thermally-controlled fluid constructed so as to circulate through said pad.

29. The device of claim 25, where said environmental control unit further comprises a temperature probe, said temperature probe constructed so as to measure the temperature of air circulating within said transportable life support system.

30. The device of claim 29, where said temperature probe is selected from a group consisting of a thermocouple and a thermistor.

31. A transportable life support system comprising:

a) a base including:

i) a ventilator having a means for supplying and maintaining delivery of air, said means constructed so as to direct air down a patient's trachea and lungs, said ventilator may or may not have a carbon dioxide scrubber constructed so as to remove carbon dioxide from expired air when rebreathing of carbon dioxide may be a hazard, a means for filtering intake and exhaust air of contaminants, said ventilator constructed so as to ventilate said patient;

ii) an oxygen source connected to said ventilator, said oxygen source constructed so as to provide oxygen to said patient;

iii) a environmental control unit having a means for providing contaminant-free air to the unit, said unit constructed so as to control said patient's temperature;

iv) a suction unit constructed so as to remove unwanted fluids from the patient;

v) a defibrillator constructed so as to provide cardioversion for life threatening arrhythmias;

vi) a monitor comprising a touch screen constructed so as to display any vital signs of the patient;

vii) a receiver/transmitter connected to said monitor, said receiver/transmitter constructed so as to transmit information to, and receive information from, a remote location;

viii) a pulse-oximetry sensor constructed so as to measure the patient's hemoglobin oxygen saturation level;

ix) an electrocardiogram sensor constructed so as to monitor the patient's heart rate;

x) an oscillometric blood pressure sensor constructed so as to monitor the patient's blood pressure;

xi) an inspired/expired oxygen sensor constructed so as to measure oxygen levels with the patient's airway;

xii) a carbon dioxide sensor constructed so as to measure carbon dioxide levels within the patient's airway and further constructed so as to validate proper placement or patency of an endotracheal tube positioned in the patient's airway;

xiii) an airway pressure sensor constructed so as to measure airway pressure and provide feedback to the ventilator in order to prevent the deleterious effects of hyperinflation;

xiv) an iv infusion pump constructed to provide a resuscitation fluid to the patient;

xv) a drug infusion pump constructed to provide medications to the patient;

xvi) an on-board computer connected to said ventilator said oxygen source, said environmental control unit, said monitor, said receiver/transmitter, said pulse-oximetry sensor, said electrocardiogram sensor, said oscillometric blood pressure sensor, said inspired/expired oxygen sensor, said carbon dioxide sensor, said airway pressure sensor, said iv infusion pump and said drug infusion pump so as to control care administered to the patient;

wherein said inspired/expired oxygen sensor and pulse oximetry sensor constructed so as to guide oxygen delivery to said patient; and xvii) a power source constructed to operate said ventilator, said oxygen source, said environmental control unit, said suction unit, said defibrillator, said on-board computer, said monitor, said receiver/transmitter, said pulse oximetry sensor, said electrocardiogram sensor, said oscillometric blood pressure sensor, said inspired/expired oxygen sensor, said carbon dioxide sensor, said airway pressure sensor, said iv infusion pump and said drug infusion pump;

b) a stretcher removably attached to the base; and c) a canopy connected to the base said canopy and base constructed so as to form a fluid impermeable seal.

32. The device of claim 31, wherein said means for supplying and maintaining delivery of air is selected from a group consisting of a laryngeal mask airway and an endotracheal tube.

33. The device of claim 32, wherein said means for filtering intake and exhaust air of contaminants in said ventilator and said means for providing contaminant-free air to the environmental control unit comprise at least one NBC type filter.

34. The device of claim 33, wherein said oxygen source is an oxygen generator.

35. The device of claim 34, where said environmental control unit further comprises a body temperature sensor.

36. The device of claim 35, where said body temperature sensor is selected from a group consisting of an axillary probe, a rectal probe, and a tympanic sensor.

37. The device of claim 36, wherein said power source further comprises at least one rechargeable battery and a connector constructed so as to receive external power and where said connector is connected to said at least one battery.

38. The device of claim 37, wherein said canopy comprises a hard shell.

39. The device of claim 38, where said environmental control unit comprises a heating/cooling pad.

40. The device of claim 39, where said heating/cooling pad further comprises a temperature sensor, said temperature sensor constructed so as to provide said on-board computer with a temperature reading of said heating/cooling pad.

41. The device of claim 40, where said heating/cooling pad further includes a thermally-controlled fluid constructed so as to circulate through said pad.

42. The device of claim 38, where said environmental control unit further comprises a temperature probe, said temperature probe constructed so as to measure the temperature of air circulating within said transportable life support system.

43. The device of claim 42, where said temperature probe is selected from a group consisting of a thermocouple and a thermistor.

44. A transportable life support system comprising:

a) a base including:

i) a ventilator having a means for supplying and maintaining delivery of air, said means constructed so as to direct air down a patient's trachea and lungs, said ventilator may or may not have a carbon dioxide scrubber constructed so as to remove carbon dioxide from expired air when rebreathing of carbon dioxide may be a hazard, a means for filtering intake and exhaust air of contaminants, said ventilator constructed so as to ventilate said patient;

ii) an oxygen source connected to said ventilator, said oxygen source constructed so as to provide oxygen to said patient;

iii) an environmental control unit having a means for providing contaminant-free air to the unit, said unit constructed so as to control said patient's temperature;

iv) a suction unit constructed so as to remove unwanted fluids from the patient;

v) a defibrillator constructed so as to provide cardioversion to connect life threatening arrhythmias;

vi) a monitor comprising a touch screen constructed so as to display any vital signs of the patient;

vii) a receiver/transmitter connected to said monitor, said receiver/transmitter constructed so as to transmit information to, and receive information from, a remote location;

viii) a pulse-oximetry sensor constructed so as to measure the patient's hemoglobin oxygen saturation level;

ix) an electrocardiogram sensor constructed so as to monitor the patient's heart rate;

x) an oscillometric blood pressure sensor constructed so as to monitor the patient's blood pressure;

xi) an inspired/expired oxygen sensor constructed so as to measure oxygen levels with the patient's airway;

xii) a carbon dioxide sensor constructed so as to measure carbon dioxide levels within the patient's airway and further constructed so as to validate proper placement or patency of an endotracheal tube positioned in the patient's airway;

xiii) an airway pressure sensor constructed so as to measure airway pressure and provide feedback to the ventilator in order to prevent the deleterious effects of hyperinflation;

xiv) an iv infusion pump constructed to provide a resuscitation fluid to the patient; and xv) a drug infusion pump constructed to provide medications to the patient;

xvi) an on-board computer connected to said ventilator said oxygen source, said environmental control unit, said monitor, said receiver/transmitter, said pulse-oximetry sensor, said electrocardiogram sensor, said oscillometric blood pressure sensor, said inspired/expired oxygen sensor, said carbon dioxide sensor, said airway pressure sensor, said iv infusion pump and said drug infusion pump so as to control care administered to the patient;

wherein said inspired/expired oxygen sensor and pulse oximetry sensor constructed so as to guide oxygen delivery to said patient;

xvii) a power source constructed to operate said ventilator, said oxygen source, said environmental control unit, said suction unit, said defibrillator, said on-board computer, said monitor, said receiver/transmitter, said pulse oximetry sensor, said electrocardiogram sensor, said oscillometric blood pressure sensor, said inspired/expired oxygen sensor, said carbon dioxide sensor, said airway pressure sensor, said iv infusion pump and said drug infusion pump;

b) a stretcher removably attached to the base; and c) a canopy connected to the base said canopy and base constructed so as to form a fluid impermeable 'seal.

45. The device of claim 44, wherein said means for supplying and maintaining delivery of air is selected from a group consisting of a laryngeal mask airway and an endotracheal tube.

46. The device of claim 45, wherein said means for filtering intake and exhaust air of contaminants in said ventilator and said means for providing contaminant-free air to the environmental control unit comprise at least one NBC type filter.

47. The device of claim 46, wherein said oxygen source is an oxygen generator.

48. The device of claim 47, where said environmental control unit further comprises a body temperature sensor.

49. The device of claim 48, where said body temperature sensor is selected from a group consisting of an axillary probe, a rectal probe, and a tympanic sensor.

50. The device of claim 49, wherein said power source further comprises at least one rechargeable battery and a connector constructed so as to receive external power and where said connector is connected to said at least one battery.

51. The device of claim 50, wherein said canopy comprises a soft shell.

52. The device of claim 51, wherein said soft-shell canopy is opaque and constructed so as to comprise reflective and insulative properties.

53. The device of claim 52, wherein said soft-shell canopy further comprises a clear plastic window.

54. The device of claim 53, wherein said soft-shell canopy further comprises pleats.

55. The device of claim 54, wherein said soft-shell canopy further comprises at least one fastening means.

56. The device of claim 55, where said environmental control unit comprises a heating/cooling pad.

57. The device of claim 56, where said heating/cooling pad further comprises a temperature sensor, said temperature sensor constructed so as to provide said on-board computer with a temperature reading of said heating/cooling pad.

58. The device of claim 57, where said heating/cooling pad further includes a thermally-controlled fluid constructed so as to circulate through said pad.

59. The device of claim 55, where said environmental control unit further comprises a temperature probe, said temperature probe constructed so as to measure the temperature of air circulating within said transportable life support system.

60. The device of claim 59, where said temperature probe is selected from a group consisting of a thermocouple and a thermistor.

61. A method of operating a transportable life support system comprising administering aid to a patient by the steps of:

(a) placing the patient on a stretcher of said transportable life support system;

(b) covering the patient with canopy having a fluid impermeable seal;

(c) displaying the patient's vital signs on a monitor having a touch screen;

(d) respirating the patient using a ventilator;

(e) administering oxygen to the patient using the ventilator and an oxygen source;

(f) regulating the patient's body temperature using a environmental control unit;

(g) removing unwanted fluids from the patient using a suction unit;

(h) providing cardioversion to correct life threatening arrhythmias;

(i) transmitting and receiving information remotely, using a receiver/transmitter;

(j) controlling said monitor, said ventilator, and said environmental control unit using an on-board computer; and (k) operating said ventilator, said oxygen source, said environmental control unit, said suction unit, said defibrillator, said on-board computer, said monitor and said receiver transmitter using a power source.

62. The method of operating the transportable life support system as recited in claim 61, and further comprising determining arterial hemoglobin oxygen saturation using a pulse oximeter sensor.

63. The method of operating the transportable life support system as recited in claim 62, and further comprising determining the need for oxygen delivery using the on-board computer.

64. The method of operating the transportable life support system as recited in claim 63 and further comprising drawing external air into said system, combining air with oxygen obtained from said oxygen source, and delivering said air and oxygen to the patient's airway, using said ventilator.

65. The method of operating the transportable life support system as recited in claim 64, and further comprising conserving the quantity of oxygen and air required by providing air and oxygen to the patient's airway only during inspiration.

66. The method of operating the transportable life support system as recited in claim 65, and further comprising overriding said on-board computer, and manually activating said system using said monitor having said touch screen.

67. The method of operating the transportable life support system as recited in claim 66, and further comprising placing the patient on a heating/cooling pad and controlling the patient's body temperature by thermally controlling said heating/cooling pad.

68. The method of operating the transportable life support system as recited in claim 67, monitoring the pad temperature using a temperature sensor.

69. The method of operating the transportable life support system as recited in claim 68 and further comprising comparing the patient's body temperature with a set point temperature using the on-board computer, and gradually regulating temperature of the heating/cooling pad, while continuously monitoring the effect on the patient's body temperature.

70. The method of operating the transportable life support system as recited in claim 66 and further comprising controlling the patient's body temperature by regulating air circulating the patient using an air temperature probe.

71. The method of operating the transportable life support system as recited in claim 70, and further comprising determining efficiency of the air circulating around the patient, providing the on-board computer with a temperature reading of said system, comparing said temperature of said system with a set point temperature and gradually regulating said temperature of system, while continuously monitoring the effect on the patient's body temperature.

72. A method of operating a transportable life support system comprising administering aid to a patient by the steps of:

(a) placing the patient on a stretcher of said transportable life support system;

(b) covering the patient with canopy having a fluid impermeable seal;

(c) displaying the patient's vital signs on a monitor having a touch screen;

(d) respirating the patient using a ventilator;

(e) administering oxygen to the patient using the ventilator and an oxygen source;

(f) regulating the patient's body temperature using a environmental control unit;

(g) removing unwanted fluids from the patient using a suction unit;

(h) providing cardioversion to correct life threatening arrhythmias;

(i) continuously measuring arterial hemoglobin oxygen saturation level using a pulse oximetry sensor;

j) continuously monitoring the patient's heart rate using a electrocardiogram sensor;

k) periodically measuring the patient's blood pressure, using an oscillometric blood pressure;

l) calculating a person's blood pressure based upon time difference between R-wave of monitored electrocardiogram and peak of peripheral arterial wave form detected from the pulse oximetry sensor;

m) comparing the result from step viii) with the result from step vii)

n) adjusting the patient's calculated blood pressure from step xv) to conform to the patient's measured blood pressure from step xvi);

o) continuously monitoring the patient's airway oxygen level;

p) continuously monitoring the patient's carbon dioxide level;

q) continuously monitoring airway pressure in the patient's airway; and r) closed loop administration of resuscitation fluids to the patient based on continuous blood pressure measurements obtained in step xiv); and s) closed loop administration of drug therapy to the patient based on continuous blood pressure measurements obtained in step xiv).

73. The method of operating the transportable life support system as recited in claim 72, and further comprising determining the need for oxygen delivery.

74. The method of operating the transportable life support system as recited in claim 73 and further comprising drawing external air into said system, combining air with oxygen obtained from said oxygen source, and delivering said air and oxygen to the patient's airway, using said ventilator.

75. The method of operating the transportable life support system as recited in claim 74, and further comprising conserving the quantity of oxygen and air required by providing air and oxygen to the patient's airway only during inspiration.

76. The method of operating the transportable life support system as recited in claim 75, and further comprising placing the patient on a heating/cooling pad and controlling the patient's body temperature by thermally controlling said heating/cooling pad.

77. The method of operating the transportable life support system as recited in claim 76, monitoring the heating/cooling pad temperature using a temperature sensor.

78. The method of operating the transportable life support system as recited in claim 77, and further comprising comparing the patient's body temperature with a set point temperature and gradually regulating temperature of the heating/cooling pad, while continuously monitoring the effect on the patient's body temperature.

79. The method as recited in claim 78 and further comprising controlling the method by an on-board computer.

80. The method as recited in claim 78 and further comprising manually controlling the method by an attending medic or physician.

81. The method as recited in claim 80, and further comprising manually controlling iv infusion rate, drug infusion rate and settings on said ventilator using said monitor touchscreen.

82. The method as recited in claim 78, and further comprising remotely controlling the method by a remote medic or physician.

83. The method as recited in claim 78, and further comprising manually controlling the IV infusion rate, drug infusion rate and settings on said ventilator using a remote keyboard.

84. The method of operating the transportable life support system as recited in claim 75 and further comprising controlling the patient's body temperature by regulating air circulating the patient using an air temperature probe.

85. The method of operating the transportable life support system as recited in claim 84, and further comprising determining the temperature of the air circulating around the patient, comparing said temperature of said system with a set point temperature, and gradually regulating the environmental control system, while continuously monitoring the effect on the patient's body temperature.

86. The method as recited in claim 85 and further comprising controlling the method by an on-board computer.

87. The method as recited in claim 85 and further comprising manually controlling the method by an attending medic or physician.

88. The method as recited in claim 85 and further comprising manually controlling iv infusion rate, drug infusion rate and settings on said ventilator using said monitor touchscreen.

89. The method as recited in claim 85, and further comprising remotely controlling the method by a remote medic or physician.

* * * * *

UNITED STATES PATENT AND TRADEMARK OFFICE
CERTIFICATE OF CORRECTION

| | | |
|---|---|---|
| PATENT NO | : | 5,626,151 |
| DATED | : | May 6, 1997 |
| INVENTOR(S) | : | Charles Linden |

It is certified that error appears in the above-identified patent and that said Letters Patent is hereby corrected as shown below:

On the title page after [75] Inventor:
insert -- William P. Wiesmann, Bethesda; Frederick J. Pearce, Olney;
Kenward B. Johnson, Wheaton; before "Charles Linden, Bethesda," insert --
all of -- before "MD."

Signed and Sealed this

Fifteenth Day of July, 1997

*Attest:*

BRUCE LEHMAN

*Attesting Officer*       *Commissioner of Patents and Trademarks*